US 6,656,171 B1

(12) United States Patent
Matsuda et al.

(10) Patent No.: US 6,656,171 B1
(45) Date of Patent: Dec. 2, 2003

(54) FASTENER DEVICE AND DISPOSABLE PRODUCT USING THE SAME

(75) Inventors: Toshiyuki Matsuda, Akashi (JP); Limin Song, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/049,202

(22) PCT Filed: Aug. 26, 1999

(86) PCT No.: PCT/US99/19523

§ 371 (c)(1),
(2), (4) Date: Feb. 8, 2002

(87) PCT Pub. No.: WO01/13842

PCT Pub. Date: Mar. 1, 2001

(51) Int. Cl.[7] .................................................. A61F 13/15
(52) U.S. Cl. ............. 604/390; 604/385.03; 604/385.05; 156/204
(58) Field of Search ................................. 604/389, 390, 604/385.03, 385.05; 156/204

(56) References Cited

U.S. PATENT DOCUMENTS

| 4,778,701 | A |   | 10/1988 | Pape et al. |   |
|---|---|---|---|---|---|
| 4,801,480 | A |   | 1/1989 | Panza et al. |   |
| 4,959,265 | A |   | 9/1990 | Wood et al. |   |
| 6,063,066 | A | * | 5/2000 | Inoue et al. | 604/385.03 |
| 6,063,466 | A | * | 5/2000 | Tuschy et al. | 428/40.1 |
| 6,221,483 | B1 | * | 4/2001 | Hilston et al. | 428/343 |

FOREIGN PATENT DOCUMENTS

| EP | 0 780 109 A2 | 6/1997 |
| EP | 0 826 352 A2 | 3/1998 |
| EP | 0 861 642 A2 | 9/1998 |
| WO | WO-96/12464 A1 | 5/1996 |
| WO | WO-99/32059 A1 | 7/1999 |

* cited by examiner

*Primary Examiner*—Weilun Lo
*Assistant Examiner*—Michael Bogart
(74) *Attorney, Agent, or Firm*—Jack L. Oney, Jr.; Jay A. Krebs; Ken K. Patel

(57) ABSTRACT

The present invention is directed to a fastener device. The fastener device includes a first tape section having a free end portion and a first connection portion opposing the free end portion; a second tape section having a second connection portion and a first anchor portion opposing the second connection portion The second connection portion is joined to the first connection portion of the first tape section. The fastener device further includes a third tape section having a third connection portion and a second anchor portion next to the third connection portion. The third connection portion is joined to the second connection portion of the second tape section. The third connection portion is joined to a branch connection portion between the second connection portion and the first anchor portion of the second tape section. The present invention is also directed to a disposable product which employs the fastener device. The present invention is further directed to a disposable pull-on garment which employs the fastener device as a disposal device.

7 Claims, 4 Drawing Sheets

FASTENER DEVICE AND DISPOSABLE PRODUCT USING THE SAME

FIELD

The present invention relates to fastener devices and disposable products using the same. Examples of such disposable products include sweat bands, bandages, body wraps, disposable garments including disposable diapers (adult and baby), and disposable absorbent pads including sanitary napkins and incontinence devices. The present invention has a particular applicability to disposable pull-on garments such as pull-on diapers, training pants, incontinent briefs, and the like.

BACKGROUND

Fastener devices have previously been used in a variety of disposable products, including sweat bands, bandages, body wraps, and disposable garments including disposable diapers, and disposable absorbent pads including sanitary napkins and incontinence devices. Fastener devices are often provided in such products and used for joining a part of the product to another member (which may be provided within or outside the products). The fastener devices include a securing means which can mechanically or adhesively secure one member to another member.

One example of application of fastener devices is a waist fastener device which is often used in disposable diapers. In this example, the fastener device is used for fastening between the front panel and back ear panels (or side panels) of diapers. Examples of such fastener devices are disclosed, for example, in U.S. Pat. No. 3,848,594 issued to Buell on Nov. 19, 1974.

Another example of application of fastener devices is a disposal device which is used for securing a soiled pull-on garment in a convenient disposal configuration after the pull-on garment has been soiled. In this example, the fastener device (or the disposal device) is provided on the garment-facing surface of a backsheet. The convenient disposal configuration is achieved by securing a part of the backsheet to the other part of the backsheet through the fastener device. Examples of such fastener devices are disclosed, for example, in International Publication No. WO 94/09736 (Rollag et al.) published on May 11, 1994 and European Patent Publication No. 0623330A2 (Hayase et al.) published on Nov. 9, 1994.

As is noted in the above, the fastener devices are often provided in disposable products (or garments) and can be used in different manners. It is generally expected that the fastener devices are firmly secured to the disposable products, otherwise they tend to be separated from the disposable products by a force which may be externally (and sometimes accidentally) applied during the use of the product. For example, when a fastener device is used in a disposable pull-on garment as a disposal device, it is secured to the garment-facing surface of the backsheet. Recently there is a trend that the disposable pull-on garments often have an outer cover nonwoven fabric which covers the entire garment-facing surface of the backsheet to provide a cloth-like garment feel. It has been discovered that users of the disposable pull-on garments tend to prefer a soft touch of such an outer cover nonwoven fabric. It is generally noted that soft nonwoven fabric tend :to have a weak mechanical strength. The disposal device is attached to the outer cover nonwoven fabric in the disposable pull-on garments. As a result, the disposal device tends to be more easily separated from the outer cover nonwoven fabric during use. In particular, in the operation of pulling the grip tab of the disposal device to extend the preliminary folded tape sections (normally just before the actual use of the disposal device), the portion which secures the disposal device to the outer cover nonwoven fabric tends to be easily torn thereby causing an undesirable separation of the disposal device from the disposable pull-on garment.

Based on the foregoing, there is a need for a fastener device which can be more firmly secured to disposable products.

SUMMARY

The present invention is directed to a fastener device. The fastener device includes a first tape section having a free end portion and a first connection portion opposing the free end portion; a second tape section having a second connection portion and a first anchor portion opposing the second connection portion. The second connection portion is joined to the first connection portion of the first tape section. The fastener device further includes a third tape section having a third connection portion and a second anchor portion next to the third connection portion. The third connection portion is joined to the second connection portion of the second tape section. The third connection portion is joined to a branch connection portion between the second connection portion and the first anchor portion of the second tape section.

The present invention is also directed to a disposable product which employs the fastener device.

The present invention is further directed to a disposable pull-on garment which employs the fastener device as a disposal device.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

DETAILED DESCRIPTION

All cited references are incorporated herein by reference in their entireties. Citation of any reference is not an admission regarding any determination as to its availability as prior art to the claimed invention.

Herein, "comprise" means that other element(s) and step(s) which do not affect the end result can be added. These terms encompass the terms "consisting of" and "consisting essentially of".

Herein, "pull-on garment" refers to articles of wear which have a defined waist opening and a pair of leg openings and which are pulled onto the body of the wearer by inserting the legs into the leg openings and pulling the article up over the waist.

Herein, "disposable" describes garments which are not intended to be laundered or otherwise restored or reused as a garment (i.e., they are intended to be discarded after a single use and, preferably, to be recycled, composted or otherwise disposed of in an environmentally compatible manner).

Herein, "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like.

Herein, "panel" denotes an area or element of the pull-on garment. (While a panel is typically a distinct area or element, a panel may coincide (functionally correspond) somewhat with an adjacent panel.)

Herein, "layer" does not necessarily limit the element to a single strata of material in that a layer may actually comprise laminates or combinations of sheets or webs of the requisite type of materials.

Herein, "joined" or "joining" encompasses configurations whereby an element is directly secured to another by affixing the element directly to the other element, and configurations whereby the element is indirectly secured to the other element by affixing the element to intermediate member(s) which in turn are affixed to the other element.

Herein, "uncontracted state" is used to describe states of pull-on garments in its unseamed (i.e., seams are removed), flat and relaxed condition wherein all elastic materials used are removed therefrom.

Figure 1:
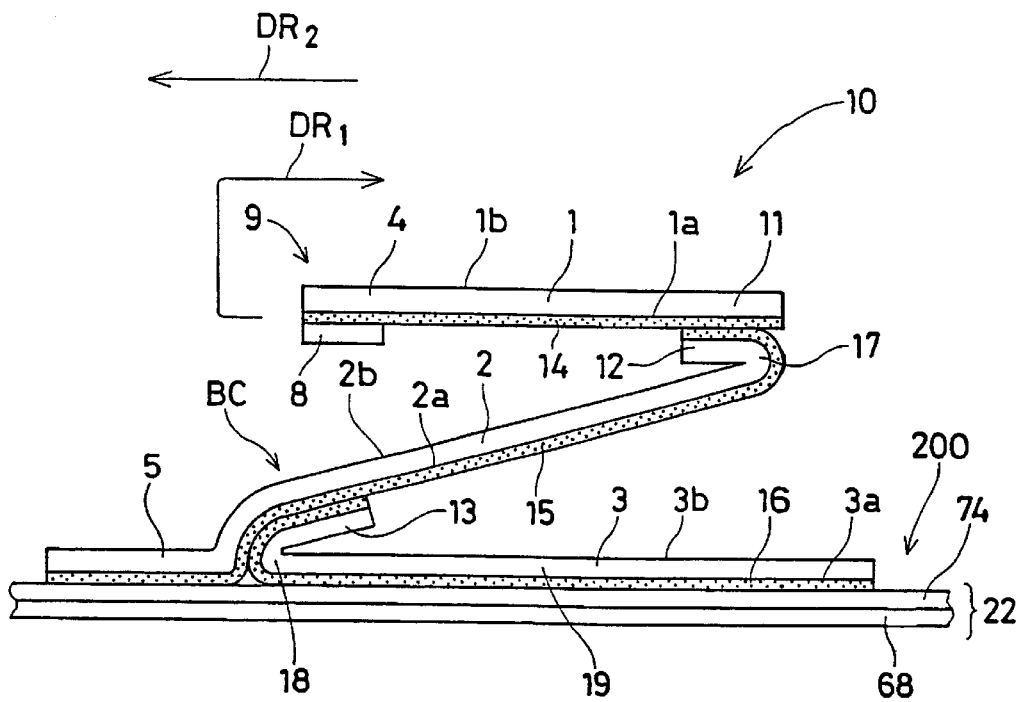
FIG. 1 is a cross-sectional view of a preferred embodiment of the fastener device of the present invention.

FIG. 1 is a cross-sectional view of a preferred embodiment of the fastener device 10 of the present invention. This fastener device 10 can be provided on any disposable product 200 which needs to have a fastening mechanism. When the fastener device 10 is used in a disposable garment, it is preferably provided on a backsheet 22 of the garment (or the product 200) which preferably includes an outer cover nonwoven layer 74 and a liquid impervious plastic film 68. Thus, FIG. 1 shows a part of such a backsheet 22 as well as the fastener device 10. (The disposable product 200 which the present invention can be applied to will be described in detail hereinafter.)

Referring to FIG. 1, the fastener device 10 includes first, second and third tape sections 1, 2 and 3 which are connected together. Although the first, second and third tape sections 1, 2 and 3 are shown as being spaced apart each other in FIG. 1, practically they are folded and piled (or layered) together before the fastener device 10 is actually used for fastening.

The first, second and third tape sections 1, 2 and 3 may be formed by a thin plastic film, a paper or a nonwoven material. In a preferred embodiment, each of the first, second and third tape sections 1, 2 and 3 is formed by a thin polypropylene film. A preferred polypropylene film is available from Minnesota Mining and Manufacturing Company, St. Pual, Minn., U.S.A., under Code No. BOPP, CPP.

The first tape section 1 has a free end portion 4 and a first connection portion 11 opposing the free end portion 4. The first tape section 1 also has an inner surface (i.e., an adhesive surface) $1a$ and an outer surface (i.e., a low adhesion surface) $1b$ opposing the inner surface $1a$. The inner surface $1a$ is coated with an adhesive material 14, while the outer surface $1b$ is coated with a low adhesion material for release treatment (not shown in FIG. 1). The adhesive material 14 on one hand firmly adheres to the inner surface $1a$ of the first tape section 1, and the other hand is adapted to be attached and re-attached to other component (not shown in FIG. 1) to which a fastening is required in the disposable product 200. The adhesive material 14 provided at the first connection portion is used to connect the first tape section 1 to the second tape section 2. The adhesive material 14 is used to keep the inner surface $1a$ of the first tape section 1 adhering to the second tape section 2 with an appropriate adhesion strength before the fastener device 10 is unfolded. A preferred adhesive material for the material 14 is a pressure-sensitive adhesive which has a basis weight of from about 10 $g/m^2$ to about 50 $g/m^2$, more preferably from about 20 $g/m^2$ to about 40 $g/m^2$. In a preferred embodiment, the adhesive material 14 has a basis weight of about 35 $g/m^2$.

In a preferred embodiment, the inner surface $1a$ at the free end portion 4 is free of adhesive so that it can form a grip tab for picking it up and gripping it by user's fingers to extend the tape sections 1, 2 and 3. Alternatively and more preferably, the adhesive coating portion at the free end portion 4 is provided with a thin film strip material 8 which covers or masks the adhesive to form the grip tab 9 as shown in FIG. 1. Yet alternatively, the grip tab 9 can be formed by folding over the free end portion 4 to the inner surface $1a$ of the first tape section 1, and attaching it to itself (not shown in FIG. 1).

The second tape section 2 has a second connection portion 12 and a first anchor portion 5 opposing the second connection portion 12. The second connection portion 12 is the portion that is used to connect the second tape section 2 to the first tape section 1. The first anchor portion 5 is the portion that is used to secure a part of the second tape section 2 to the product 200. The second tape section 2 has a first surface (i.e., an adhesive surface) $2a$ and a second surface (i.e., a low adhesion surface) $2b$ opposing the first surface $2a$. The first surface $2a$ is coated with an adhesive material 15, while the second surface $2b$ is coated with (or release treated with) a low adhesion material (not shown in FIG. 1). The second connection portion 12 is turned over towards the first tape section 1 so that a fold 17 is formed. The first and second tape sections 1 and 2 are connected through the adhesives provided at the first and second connection portions 11 and 12. The first anchor portion 5 of the second tape section 2 is secured to a part of the product 200 through the adhesive material 15, i.e., the adhesive material 15 needs to keep the first anchor portion 5 of the second tape section 2 secured to the part of the product 200. The adhesive material 15 also needs to keep the first surface $2a$ of the second tape section 2 adhering to the third tape section 3 with an appropriate (or not too strong) adhesion strength before the fastener device 10 is unfolded. A preferred adhesive material for the material 15 is a pressure-sensitive adhesive which has a basis weight of from about 10 $g/m^2$ to about 25 $g/m^2$, more preferably from about 15 $g/m^2$ to about 20 $g/m^2$. In a preferred embodiment, the adhesive material 15 has a basis weight of about 17 $g/m^2$.

Referring again to FIG. 1, the third tape section 2 has a third connection portion 13 and a second anchor portion 19 which is preferably positioned next to the third connection portion 13. The third tape section 3 has a first surface (i.e., an: adhesive surface) $3a$ and a second surface (i.e., a low adhesion surface) 3b opposing the first surface 3a. The first surface 3a is coated with an adhesive material 16, while the second surface 3b is coated with (or release treated with) a low adhesion material (not shown in FIG. 1). The third connection portion 13 is turned over towards the second tape section 2 so that a fold 18 is formed. The third tape section 3 is connected to a branch connection portion BC which is chosen from the intermediate area between the second connection portion 12 and the first anchor portion of the second tape section 2. Preferably, the branch connection portion BC is positioned closer to the first anchor portion 5 than the second connection portion 12, more preferably right next to the first anchor portion 5 as shown in FIG. 1.

The second anchor portion 19 of the third tape section 3 adheres to another part of the product 200 through the adhesive material 16. Consequently, the fastener device 10 is firmly secured to the product 200 through the anchor portions 5 and 19. A preferred adhesive material for the material 16 is a pressure-sensitive adhesive which has a basis weight of from about 10 $g/m^2$ to about 50 $g/m^2$, more preferably from about 30 $g/m^2$ to about 40 $g/m^2$. In a preferred embodiment, the adhesive material 16 has a basis weight of about 35 $g/m^2$.

Figure 2:
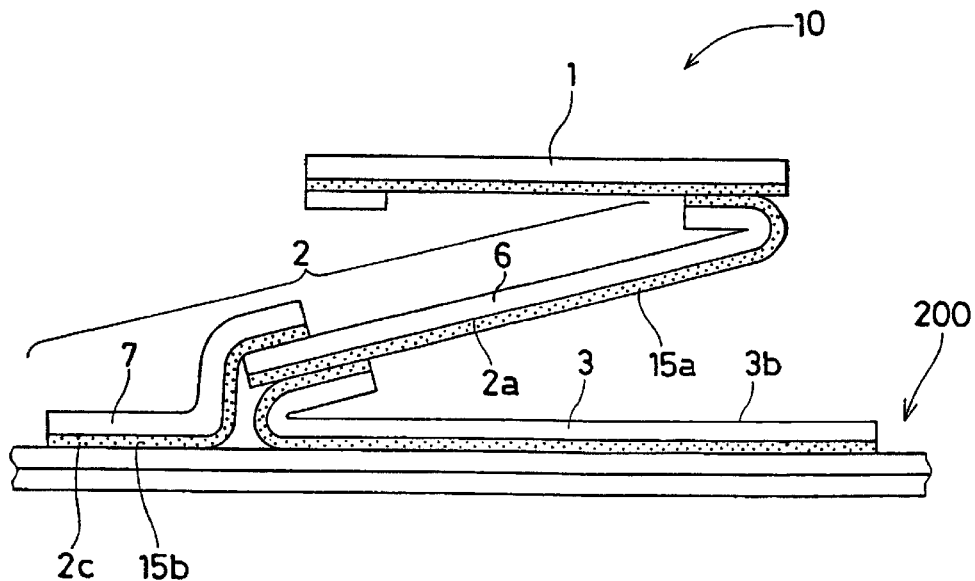
FIG. 2 is a cross-sectional view of another preferred embodiment of the fastener device.

As shown in FIG. 1, the second tape section 2 is preferably formed by a unitary member of a plastic film, a paper or a nonwoven material. Alternatively, the second tape section 2 can be formed by two (or more) separate members as shown in, for example, FIG. 2. Referring to FIG. 2, the second tape section 2 is formed by a first member 6 and a second member 7 which are connected together. The first surface 2a of the first tape member 6 is coated with an adhesive material 15a, while the first surface 2c of the second tape member 7 is coated with an adhesive material 15b. The first and second members 6 and 7 are preferably formed by the same material as that used for the other tape sections 1 and 3. The second tape section 2 shown in FIG. 2 have a similar tape structure to the second tape section 2 shown in FIG. 1 except that the second member 7 is connected between the first member 6 and the product 200 so that the second member 7 works as an anchor portion of the second tape section 2. In a preferred embodiment, the adhesive material 15b has a higher adhesion strength than that of the adhesive material 15a such that the second member 7 works as an effective anchor portion for the second tape section 2 while the first member 6 has an appropriate adhesion strength against the low adhesion surface 3b of the third tape section 3.

The low adhesion materials which are preferably used for the first, second and third tape sections 1, 2 and 3 include a silicone compound which is compatible with the adhesive materials on the tape sections 1, 2 and 3.

As is noted by the above description, since the fastener device 10 includes the second tape section 2 which is supported by the first anchor portion 5 of the second tape section 2 as well as the second anchor portion 5 of the third tape section 3, it is possible to keep the fastener device 10 firmly secured to the product 200. Thus, the fastener device 10 can be kept firmly secured to the disposable product 200 without being separated from the disposable product 200 by a force which may be externally applied (and sometimes accidentally applied) during the use of the product 200.

The fastener device of the present invention can be applied to a variety of disposable products in need of a fastening mechanism. Preferred disposable products include sweat bands, bandages, body wraps, disposable garments including disposable diapers (adult and baby), and disposable absorbent pads including sanitary napkins.

In one embodiment, the fastener device 10 is used for a waist fastening system in a disposable garment (e.g., a tape type disposable diaper). In this embodiment, the fastener device 10 is used for the fastening between the front panel and the back ear panels of the disposable garment. Such a usage of the fastener device is disclosed in, for example, U.S. Pat. No. 3,848,594 issued to Buell on Nov. 19, 1974.

In a more preferred embodiment, the fastener device 10 is used in a disposable pull-on garment (e.g., a pull-on diaper) as a disposal device. After the disposable pull-on garment is soiled by excreta, it is folded to contain the contents within the soiled pull-on garment. The folded garment is secured by the fastener device to prevent the contents in the soiled pull-on garment from leaking out. Such a usage of the fastener device in disposable pull-on garments is disclosed in, for example, International Publication No. WO 94/09736 (Rollag et al.) published on May 11, 1994 and European Patent Publication No. 0623330A2 (Hayase et al.) published on Nov. 9, 1994.

Although the fastener device of the present invention can be used as a disposal device in any type of disposable garments, one preferred embodiment is described hereinafter by applying the present invention to a specific disposable pull-on garment.

Figure 3:
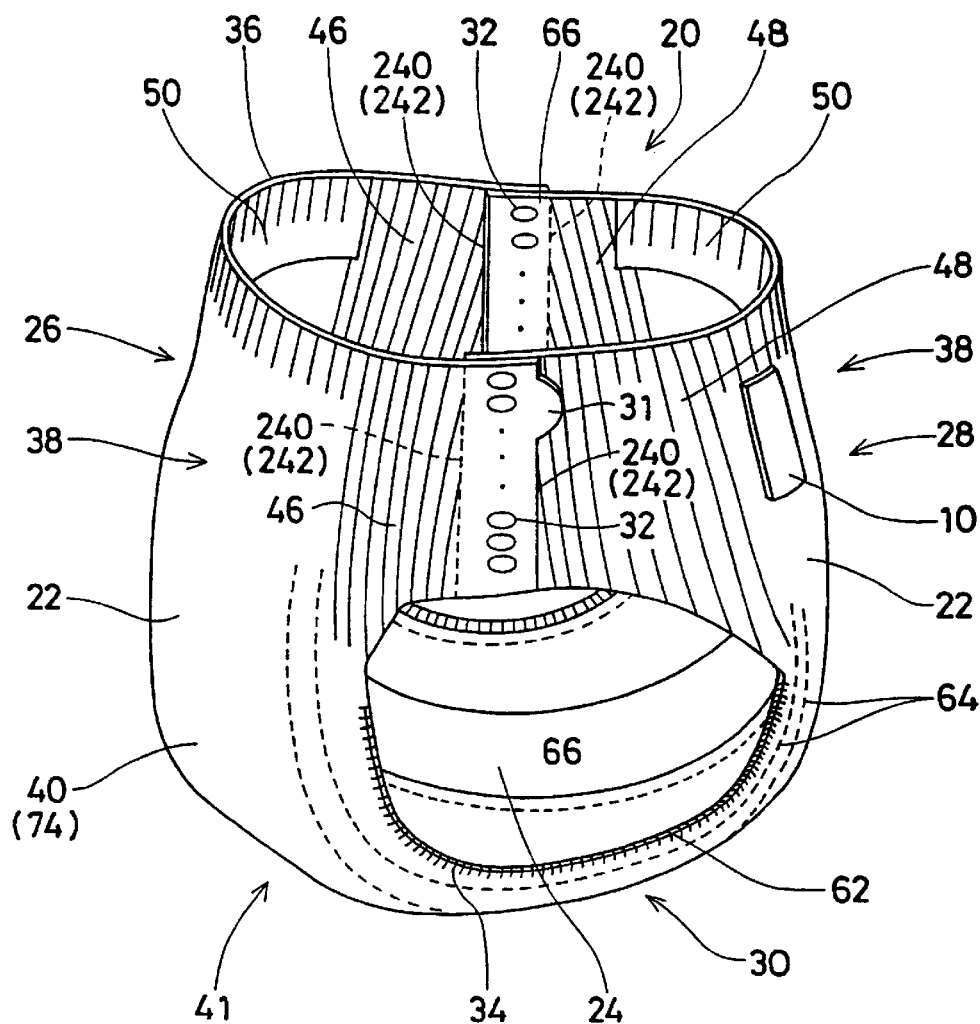
FIG. 3 is a perspective view of one preferred embodiment of the disposable pull-on garment of the present invention in a typical in use configuration.

FIG. 3 shows one preferred embodiment of a disposable pull-on garment of the present invention (e.g., a unitary disposable pull-on diaper). Referring to FIG. 3, the disposable pull-on garment 20 has a front region 26; a back region 28 and a crotch region 30 between the front region 26 and the back region 28. A chassis 41 is provided in the front, back and crotch regions 26, 28 and 30. The chassis 41 includes a liquid pervious topsheet 24, a liquid impervious backsheet 22 associated with the topsheet 24, and an absorbent core 25 (not shown in FIG. 3) disposed between the topsheet 24 and the backsheet 22.

The disposable pull-on garment 20 further includes a pair of front ear panels 46 each extending laterally outward from the corresponding sides of the chassis 41 in the front region 26, and a pair of extensible back ear panels 48 each extending laterally outward from the corresponding sides of the chassis 41 in the back region 28. Each of the ear panels 46 and 48 has an outermost edge 240 which forms an outermost edge line 242. At least one of the outermost edge lines 242 has a nonuniform lateral distance LD from the longitudinal center line 100 (not shown in FIG. 3 but in FIG. 4) in the uncontracted state of the garment 20. The pull-on garment 20 further includes seams 32 each joining the front and back ear panels 46 and 48 along the corresponding edge lines 242 to form the two leg openings 34 and the waist opening 36.

In preferred embodiments, the pull-on garment 20 includes a chassis layer 40 which generally determines the overall shape of the pull-on garment 20. In the embodiment shown in FIG. 3, the chassis layer 40 is an outer cover nonwoven layer 74 which covers all of the garment-facing surface of the pull-on garment 20 to provide the feel and appearance of a cloth garment. Preferably, the outer cover nonwoven layer 74 is a continuous sheet or web formed by a nonwoven material. The continuous sheet (i.e., the outer cover nonwoven layer 74) defines the front region 26, the back region 28 and the crotch region 30 between the front region 26 and the back region 28. Each of the ear panels 46 and 48 includes a portion of the chassis layer 40. Preferred pull-on garments which includes such a continuous sheet 30 are disclosed in U.S. Pat. No. 5,569,234 issued to Buell et al. on Oct. 29, 1996.

In a preferred embodiment, at least one pair of, more preferably both of, the pairs of the ear panels 46 and 48 are elastically extensible only in the lateral direction. In an alternative embodiment, the ear panels 46 and 48 can be elastically extensible both in the lateral and longitudinal directions. Herein, "extensible" refers to materials that are capable of extending in at least one direction to a certain degree without undue rupture. Herein, "elasticity" and "elastically extensible" refer to extensible materials that have the ability to return to approximately their original dimensions after the force that extended the material is removed. Herein, any material or element described as "extensible" may also be elastically extensible unless otherwise provided. The extensible ear panels 46 and 48 provide a more comfortable and contouring fit by initially conformably fitting the pull-on garment 20 to the wearer and sustaining this fit throughout the time of wear well past when the pull-on garment has been loaded with exudates since the ear panels 46 and/or 48 allow the sides of the pull-on garment to expand and contract.

The ear panels 46 and 48 may be formed by unitary elements of the pull-on garment 20 (i.e., they are not separately manipulative elements secured to the pull-on garment 20, but rather are formed from and are extensions of one or more of the various layers of the pull-on garment). In a preferred embodiment, the ear panels 46 and 48 include at least one unitary element or a continuous sheet (e.g. the chassis layer 40). that forms a part of the chassis 41 and continuously extends into the ear panels 46 and 48. Alternatively, the ear panels 46 and 48 may only include discrete members (not shown in Figures.) which do not have any unitary element that also forms a part of the chassis 41. Such an ear panel structure may be formed by joining the discrete members to the corresponding sides of the chassis 41.

In a preferred embodiment, the pull-on garment 20 further includes seam panels 66 each extending laterally outward from each of the ear panels 46 and 48; and tear open tabs 31 each extending laterally outward from the seam panel 66. In a preferred embodiment, each of the seam panels 66 is an extension of the corresponding ear panels 46 and 48, or at least one of the component elements used therein (e.g., the chassis; layer 40), or any other combination of the elements. More preferably, each of the tear open tabs 31 is also an extension of the corresponding seam panel 66 or at least one of its component elements used therein (e.g., the chassis layer 40), or any other combination of its elements.

In a preferred embodiment, the corresponding edge portions of the ear panels 46 and 48 are joined through the seam panels 66 in an overlapping manner to make an overlapped seam structure as shown in FIG. 3. Alternatively, the front and ear panels 46 and 48 can be seamed in a butt seam manner (not shown in Figures.).

The bonding of the seams 32 can be performed by any suitable means known in the art appropriate for the specific materials employed in the ear panels 46 and 48. Thus, sonic sealing, heat sealing, pressure bonding, adhesive or cohesive bonding, sewing, autogeneous bonding, and the like may be appropriate techniques. Preferably, the seam panels 66 are joined by a predetermined pattern of heat/pressure or ultrasonic welds which withstands the forces and stresses generated on the garment 20 during wear. A preferred method for making the seams is disclosed in WO 98/22285 (Schmitz) published on May 28, 1998.

A continuous belt 38 is formed by the ear panels 46 and 48, and a part of the chassis 41 about the waist opening 36 as shown in FIG. 3. Preferably, elasticized waist bands 50 are provided in both the front region 26 and the back region 28. The continuous belt 38 acts to dynamically create fitment forces in the pull-on garment 20 when positioned on the wearer, to maintain the pull-on garment 20 on the wearer even when loaded with body exudates thus keeping the absorbent core 25 (not shown in FIG. 3) in close proximity to the wearer, and to distribute the forces dynamically generated during wear about the waist thereby providing supplemental support for the absorbent core 25 without binding or bunching the absorbent core 25.

A fastener device 10 is provided on the backsheet 22. Specifically, the fastener device 10 is secured to the outer cover nonwoven fabric 74 (not shown in FIG. 3) of the backsheet 22. Preferably, the fastener device 10 is positioned on the longitudinal centerline 100 (not shown in FIG. 3 but FIG. 4) in the back region 28 of the backsheet 22. Alternatively (but less preferably), the fastener device 10 can be positioned at any location of the backsheet 22 as long as it can work as a disposal device.

Figure 4:
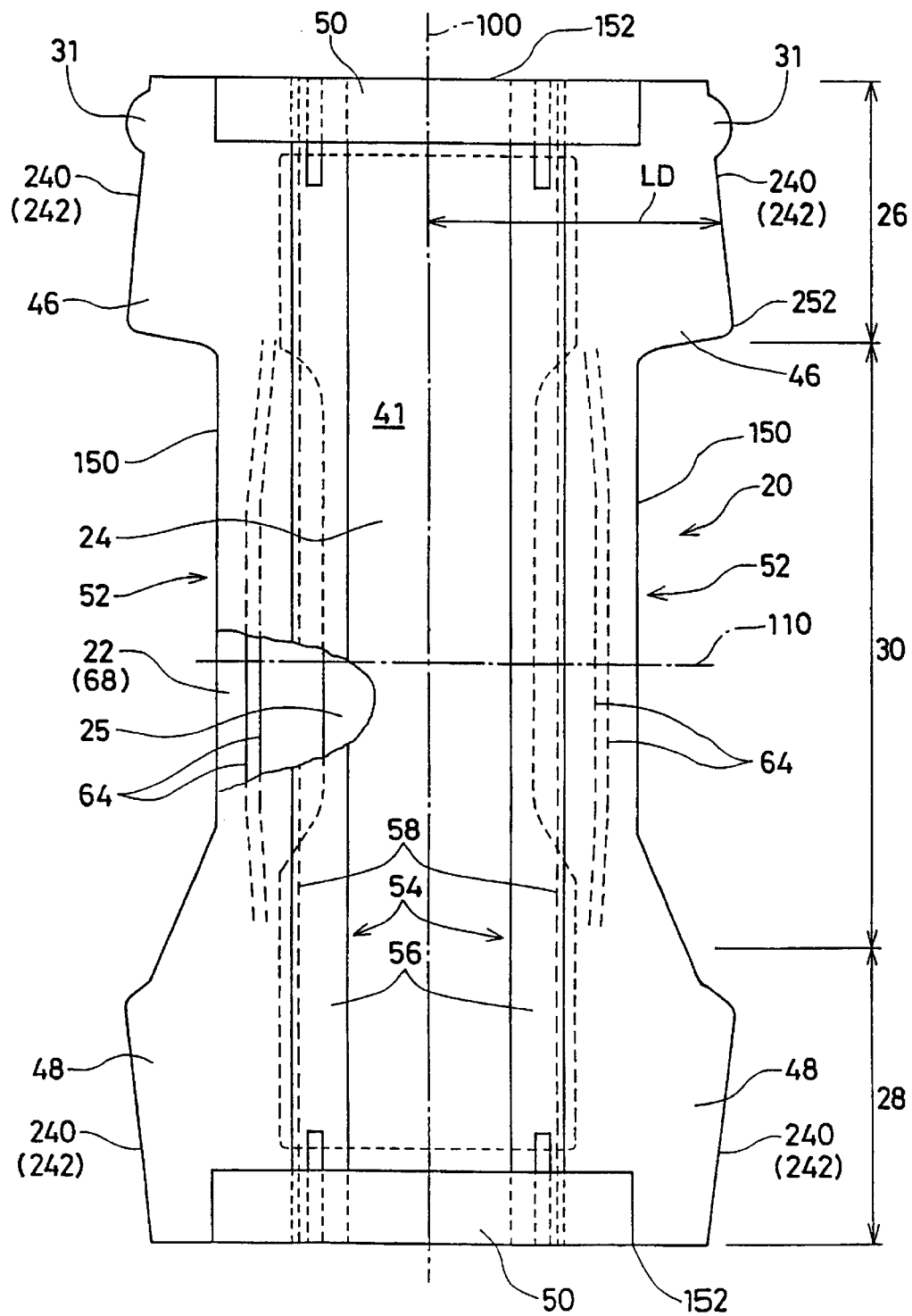
FIG. 4 is a simplified plan view of the embodiment shown in FIG. 3 in its flat uncontracted condition showing the body-facing side the garment.

FIG. 4 is a partially cut-away plan view of the pull-on garment 20 of FIG. 3 in its uncontracted state (except in the ear panels 46 and 48 which are left in their relaxed condition) with the topsheet 24 facing the viewer, prior to the ear panels 46 and 48 being joined together by the seams 32. The pull-on garment 20 has the front region 26, the back region 28 opposed to the front region 26, the crotch region 30 positioned between the front region 26 and the back region 28, and a periphery which is defined by the outer perimeter or edges of the pull-on garment 20 in which the side edges are designated 150 and 240, and the end edges or waist edges are designated 152. The topsheet 24 has the body-facing surface of the pull-on garment 20 which is positioned adjacent to the wearer's body during use. The backsheet 22 has the garment-facing surface of the pull-on garment 20 which is positioned away from the wearer's body. The pull-on garment 20 includes the chassis 41 including the liquid pervious topsheet 24, the liquid impervious backsheet 22 associated with the topsheet 24, and the absorbent core 25 positioned between the topsheet 24 and the backsheet 22. The garment 20 further includes the front and back ear panels 46 and 48 extending laterally outward from the chassis 41, the elasticized leg cuffs 52, and the elasticized waistbands 50. The topsheet 24 and the backsheet 22 have length and width dimensions generally larger than those of the absorbent core 25. The topsheet 24 and the backsheet 22 extend beyond the edges of the absorbent core 25 to thereby form the side edges 150 and the waist edges 152 of the garment 20. The liquid impervious backsheet 22 preferably includes a liquid impervious plastic film 68. The pull-on garment 20 further includes the front ear panels 46 each extending laterally outward from the chassis 41, and an inner barrier cuffs 54.

The pull-on garment 20 also has two centerlines, a longitudinal centerline 100 and a transverse centerline 110. Herein, "longitudinal" refers to a line, axis, or direction in the plane of the pull-on garment 20 that is generally aligned with (e.g. approximately parallel with) a vertical plane which bisects a standing wearer into left and right halves when the pull-on garment 20 is worm. Herein, "transverse" and "lateral" are interchangeable and refer to a line, axis or direction which lies within the plane of the pull-on garment that is generally perpendicular to the longitudinal direction (which divides the wearer into front and back body halves). The pull-on garment 20 and component materials thereof also have a body-facing surface which faces the skin of wearer in use and an garment-facing surface which is the opposite surface to the body-facing surface.

While the topsheet 24, the backsheet 22, and the absorbent core 25 may be assembled in a variety of well known configurations, exemplary chassis configurations are described generally in U.S. Pat. No. 3,860,003 issued to Kenneth B. Buell on Jan. 14, 1975; and U.S. Pat. No. 5,151,092 issued to Kenneth B. Buell et al. on Sep. 29, 1992.

The absorbent core 25 can be any absorbent member which is generally compressible, conformable, non-irritating to the wearer's skin, and capable of absorbing and retaining liquids such as urine and other body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may include one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the garment 20.

A preferred embodiment of the garment 20 has an asymmetric, modified hourglass-shaped absorbent core 25 having ears in the front and back waist regions 26 and 28. Other exemplary absorbent structures for use as the absorbent core 25 that have achieved wide acceptance and commercial success are described in U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,888,231 issued to Angstadt on Dec. 19, 1989; and U.S. Pat. No. 4,834,735, issued to Alemany et al. on May 30, 1989.

The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant.

In a preferred embodiment, the topsheet 24 is a nonwoven web that can provide reduced tendency for surface wetness; and consequently facilitate maintaining urine absorbed by the core 25 away from the user's skin, after wetting. One of the preferred topsheet materials is a thermobonded carded web which is available as Code No. P-8 from Fiberweb North America, Inc. (Simpsonville, S.C., U.S.A.).

In a preferred embodiment, the backsheet 22 includes the liquid impervious film 68 as shown in, for example, FIG. 3. Preferably, the liquid impervious film 68 longitudinally extends in the front, back and crotch regions 26, 28 and 30. More preferably, the liquid impervious film 68 does not laterally extend into the at least one of the ear panels 46 or 48. The liquid impervious film 68 has a body-facing surface 79 and an garment-facing surface opposing the body-facing surface 79. The liquid impervious film 68 is impervious to liquids (e.g., urine) and is preferably manufactured from a thin plastic film. However, more preferably the plastic film permits vapors to escape from the garment 20. In a preferred embodiment, a microporous polyethylene film is used for the liquid impervious film 68. A suitable microporous polyethylene film is manufactured by Mitsui Toatsu Chemicals, Inc., Nagoya, Japan and marketed in the trade as PG-P.

A suitable material for the liquid impervious film 68 is a thermoplastic film having a thickness of from about 0.012 mm (0.5 mil) to about 0.051 mm (2.0 mils), preferably including polyethylene or polypropylene. Preferably, the liquid impervious film has a basis weight of from about 5 $g/m^2$ to about 35 $g/m^2$. However, it should be noted that other flexible liquid impervious materials may be used.

The backsheet 22 further includes the outer cover nonwoven layer 74 (i.e., the chassis layer 40) which is joined with the garment-facing surface of the liquid impervious film 68 to form a laminate. The outer cover nonwoven layer 74 may be formed by any type of nonwoven material. Preferred nonwoven materials include a carded nonwoven material, spunbonded nonwoven material and a meltblown nonwoven material. In a preferred embodiment, the outer cover nonwoven layer 74 is formed by a carded nonwoven material of polypropylene which is obtainable from Vliesstoffwerk Christian Heinrich Sandler GmbH & Co. KG, Schwarzenbach/Scale, Germany, under Code No. Sawabond 4111.

The outer cover nonwoven layer 74 preferably covers all of the garment-facing surface of the pull-on garment 20 to provide a cloth-like feel and appearance to the garment 20. The outer cover nonwoven layer 74 can be joined to the liquid impervious film 68 by any suitable attachment means known in the art. For example, the outer cover nonwoven layer 74 may be secured to the liquid impervious film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

The backsheet 22 is positioned adjacent the garment-facing surface of the absorbent core 25 and is preferably joined thereto by any suitable attachment means known in the art. Specifically, the body-facing surface 79 of the liquid impervious film 68 may be secured to the absorbent core 25 by a uniform continuous layer of adhesive, a patterned layer of adhesive, or an array of separate lines, spirals, or spots of adhesive. Alternatively, the attachment means may include heat bonds, pressure bonds, ultrasonic bonds, dynamic mechanical bonds, or any other suitable attachment means or combinations of these attachment means as are known in the art.

The pull-on garment 20 further includes elasticized leg cuffs 52 for providing improved containment of liquids and other body exudates. The elasticized leg cuffs 52 may include several different embodiments for reducing the leakage of body exudates in the leg regions. (The leg cuffs can be and are sometimes also referred to as leg bands, side flaps, barrier cuffs, elastic cuffs or gasketing cuffs.) Preferred elasticized leg cuff designs are disclosed in, for example, U.S. Pat. No. 3,860,003 issued to Buell on Jan. 14, 1975; U.S. Pat. No. 4,695,278 issued to Lawson on Sep. 22, 1987; and U.S. Pat. No. 4,795,454 issued to Dragoo on Jan. 3, 1989.

While each elasticized leg cuff 52 may be configured so as to be similar to any of the leg bands, side flaps, barrier cuffs, or elastic cuffs described above, it is preferred that the elasticized leg cuff 52 includes an elastic gasketing cuff 62 with one or more elastic strands 64 as shown in FIG. 4, which is described in the above-referred U.S. Pat. Nos. 4,695,278 and 4,795,454.

Figure 5:
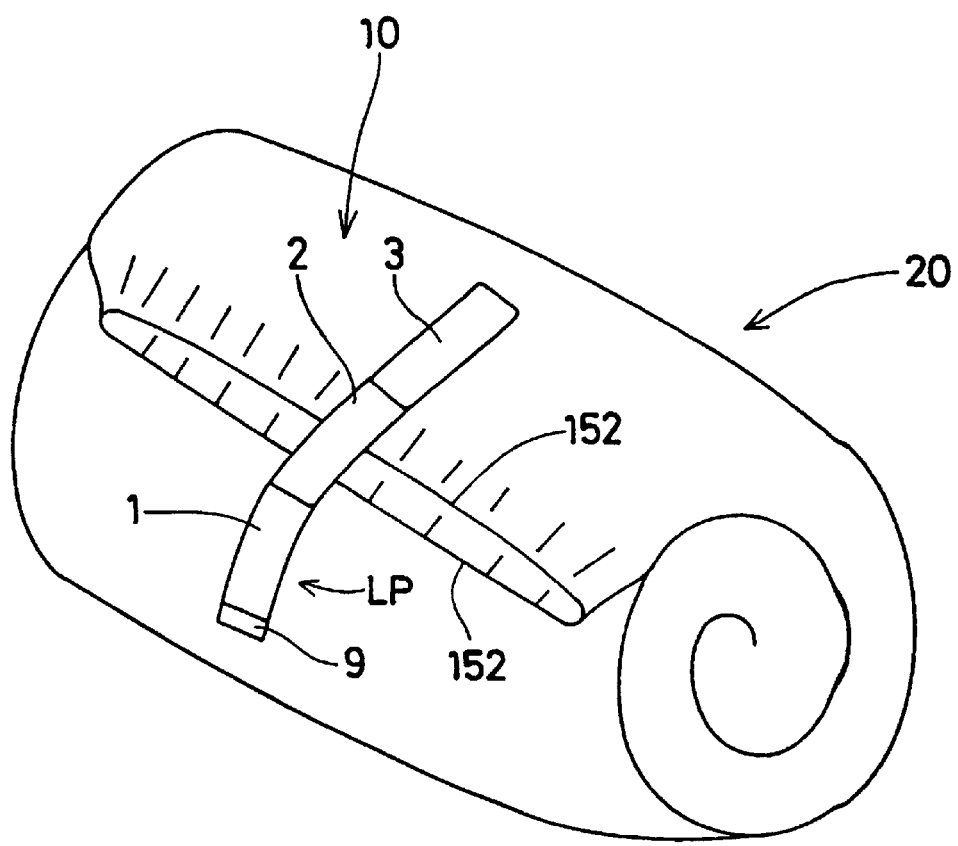
FIG. 5 is a perspective view of the pull-on garment shown in FIG. 3 when it is secured in a convenient disposal configuration.

The pull-on garment 20 preferably further includes an elasticized waistband 50 that provides improved fit and containment. The elasticized waistband 50 is that portion or zone of the pull-on garment 20 which is intended to elastically expand and contract to dynamically fit the wearer's waist. The elasticized waistband 50 preferably extends longitudinally outwardly from the waist edge of the pull-on garment 20 toward the waist edge of the absorbent core 25. Preferably, the pull-on garment 20 has two elasticized waistbands 50, one positioned in the back region 28 and one positioned in the front region 26, although other pull-on garment embodiments can be constructed with a single elasticized waistband. The elasticized waistband 50 may be constructed in a number of different configurations including those described in U.S. Pat. No. 4,515,595 issued to Kievit et al. on May 7, 1985 and the above referenced U.S. Pat. No. 5,151,092 issued to Buell. After the pull-on garment 20 has been soiled, the soiled garment 20 is tom open along the seams 32 by gripping the tear open tab 31 and the ear panel 46 or 48 to remove the soiled garment 20 from the wearer. Alternatively, if appropriate, the soiled garment 20 may be just removed from the wearer by pulling down without tearing open the seams 32. The garment 20 is then folded or rolled up by keeping the crotch portion in the center so that the 30 fastener (or disposal) device 10 can come to the outside of the rolled garment 20 for a convenient disposal as shown in FIG. 5, while containing the contents within the rolled garment 20.

Referring again to FIG. 1, the grip tab 9 of the fastener device 10 is first pulled by the user's fingers towards the direction DR1 to separate the first tape section 1 from the second surface 2b of the second tape section 2 which are initially adhered together. Since the second tape section 2 is supported by the first anchor portion 5 of the second tape section 2 as well as the second anchor portion 19 of the third tape section 3, it is possible to keep the fastener device 10 firmly secured to the backsheet 22 (or the product 200). After the grip tab 9 is pulled towards the direction DR1, then it is also pulled towards the opposite direction DR2 to separate the second tape section 2 from the second surface 3b of the third tape section 3 which are also initially adhered. At this stage, since the second tape section 2 is supported by the second anchor portion 19 of the third tape section 3 as well as the first anchor portion 5 of the second tape section 2, it is again possible to keep the fastener device firmly secured to the backsheet 22 (or the product 200).

This advantage has been becoming more important since recent disposable pull-on garments tend to use a thinner nonwoven fabric for the outer cover nonwoven layer 74 of the backsheet 22. By using the fastener device 10 which has the structure shown in FIG. 1 (or FIG. 2), the fastener device 10 can be more firmly secured to the thin outer cover nonwoven layer 74 without being separated therefrom.

The unfolded tape sections 1, 2 and 3 are them extended over the end edges 152 of the folded or rolled garment 20 so that the first tape section 1 can reach the landing position LP on the backsheet 22. The landing position LP can be any position on the backsheet 22 which can provide a convenient disposal by the fastener device 10 as shown in FIG. 5. This convenient disposal configuration can maintain the contents without leaking out.

It is understood that the examples and embodiments described herein are for illustrative purpose only and that various modifications or changes will be suggested to one skilled in the art without departing from the scope of the present invention.

What is claimed is:

1. A fastener device, comprising:
   a first tape section having a free end portion and a first connection portion opposing the free end portion;
   a second tape section having a second connection portion and a first anchor portion opposing the second connection portion, the second connection portion being joined to the first connection portion of the first tape section, the second connection portion is turned over towards the first tape section so that a first fold is formed;
   a third tape section having a third connection portion and a second anchor portion next to the third connection portion, the third connection portion being joined to the second connection portion of the second tape section, the third connection portion being joined to a branch connection portion between the second connection portion and the first anchor portion of the second tape section, the third connection portion is turned over towards the second tape section so that a second fold is formed.

2. The fastener device of claim 1, wherein the second tape section is formed by a unity member.

3. The fastener device of claim 1, wherein the adhesive is a pressure-sensitive adhesive.

4. The fastener device of claim 1, wherein the low adhesion surfaces of the second and third tape sections are treated with a silicone compound.

5. The fastener device of claim 3, wherein the pressure-sensitive adhesive of the second tape section has a basis weight of from about 10 g/m$^2$ to about 25 g/m$^2$.

6. A disposable product comprising the fastener devise of claim 1.

7. A disposable pull-on garment having two leg openings and a waist opening, comprising:
   a backsheet; and
   a disposal devise provided on the backsheet; the disposal devise including the fastener devise of claim 1;
   wherein the fastener device is joined to the backsheet through the first and second anchor portions.

* * * * *

UNITED STATES PATENT AND TRADEMARK OFFICE
CERTIFICATE OF CORRECTION

PATENT NO. : 6,656,171 B1
DATED : December 2, 2003
INVENTOR(S) : Matsuda et al.

It is certified that error appears in the above-identified patent and that said Letters Patent is hereby corrected as shown below:

Column 1,
Line 64, after the word "tend", delete ":".

Column 2,
Line 6, delete "tom" and insert -- torn --.

Column 6,
Line 66, delete "30".

Column 7,
Line 28, after "40)", delete ".".

Column 8,
Line 59, delete "worm" and insert -- worn --.

Column 11,
Line 42, delete "tom" and insert -- torn --.
Line 49, delete "30".

Column 12,
Line 47, delete "unity" and insert -- unitary --.

Signed and Sealed this

Twenty-seventh Day of April, 2004

JON W. DUDAS
*Acting Director of the United States Patent and Trademark Office*